United States Patent
McKinley

(12) 
(10) Patent No.: US 6,219,182 B1
(45) Date of Patent: Apr. 17, 2001

(54) MULTIPLE MAGNIFICATION STEREO VIDEO TELESCOPE OBJECTIVE LENS SYSTEM

(75) Inventor: Harry R. McKinley, Southampton, MA (US)

(73) Assignee: McKinley Optics, Inc., Southampton, MA (US)

( * ) Notice: Subject to any disclaimer, the term of this patent is extended or adjusted under 35 U.S.C. 154(b) by 0 days.

(21) Appl. No.: 09/322,838

(22) Filed: May 28, 1999

Related U.S. Application Data

(60) Provisional application No. 60/087,000, filed on May 28, 1998.

(51) Int. Cl.$^7$ ............................ G02B 23/00; G02B 23/12; G02B 7/16
(52) U.S. Cl. .................... 359/407; 359/421; 359/821; 359/400
(58) Field of Search .................... 359/376, 377, 359/375, 374, 373, 372, 407, 421, 744, 821, 369, 400, 381, 656–660; 396/17, 432

(56) References Cited

U.S. PATENT DOCUMENTS

| | | | |
|---|---|---|---|
| 2,901,942 | * | 9/1959 | Tackaberry ............................ 359/381 |
| 4,262,989 | * | 4/1981 | Waters .................................. 359/381 |
| 4,634,241 | * | 1/1987 | Kohayakawa et al. ............... 359/377 |
| 4,640,586 | * | 2/1987 | Iba et al. .............................. 359/377 |
| 4,657,356 | * | 4/1987 | Matsumura ........................... 359/377 |
| 5,067,804 | * | 11/1991 | Kitajima et al. ...................... 359/363 |
| 5,673,147 | * | 9/1997 | McKinley ............................. 359/376 |

* cited by examiner

Primary Examiner—Jon Henry
(74) Attorney, Agent, or Firm—McDermott, Will & Emery

(57) ABSTRACT

A stereoscopic objective lens system for video endoscopes and borescopes includes two full-diameter doublets and two lens pairs forming a stereo lens set. A rotatable dual telescope is disposed between the two doublets and the stereo lens pairs, establishing a Galilean telescope associated with each stereo channel. The Galilean telescopes are each rotatable, preferably in convert, to be in or out of alignment with the system optical axis. When out of alignment, the Galilean telescopes have no effect along the optical path. When in alignment, the Galilean telescopes provide an increase or decrease in magnification, depending on orientation of the telescopes. The full-diameter doublets present equal-angle pairs from symmetrically disposed object points to the lenses of the stereo lens pair. This equal-angle property enables accurate object/image mapping onto the final stereo image pair, such that all parts of each left/right image can be mapped to within a fraction of a video pixel to each other.

23 Claims, 16 Drawing Sheets

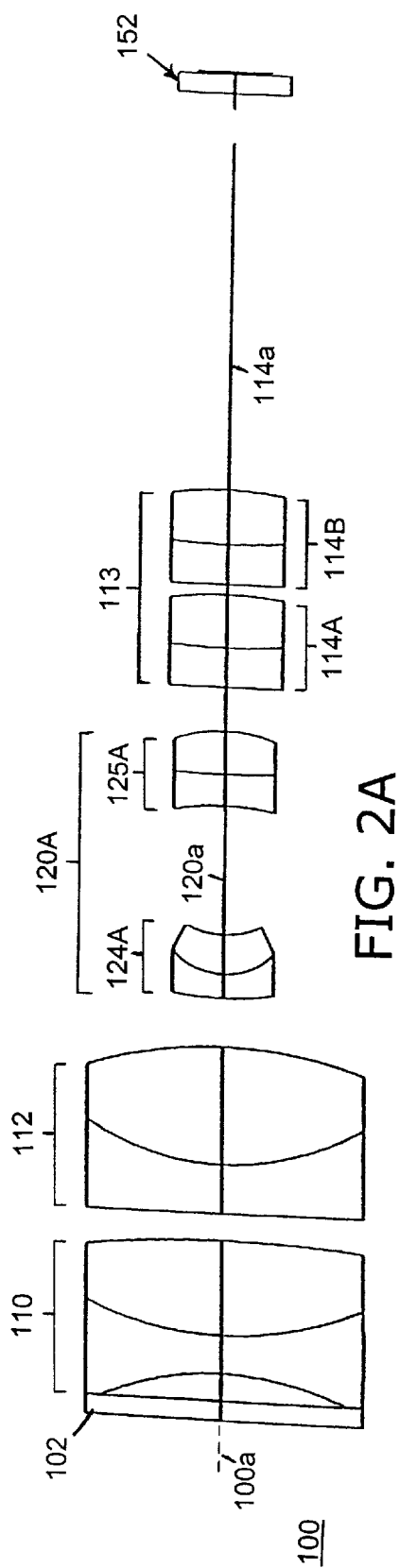
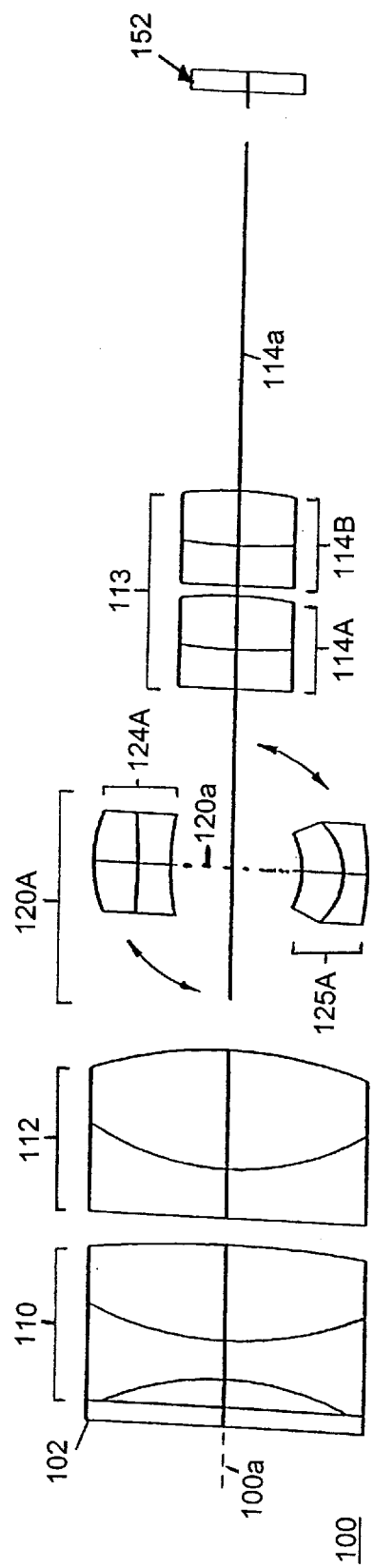

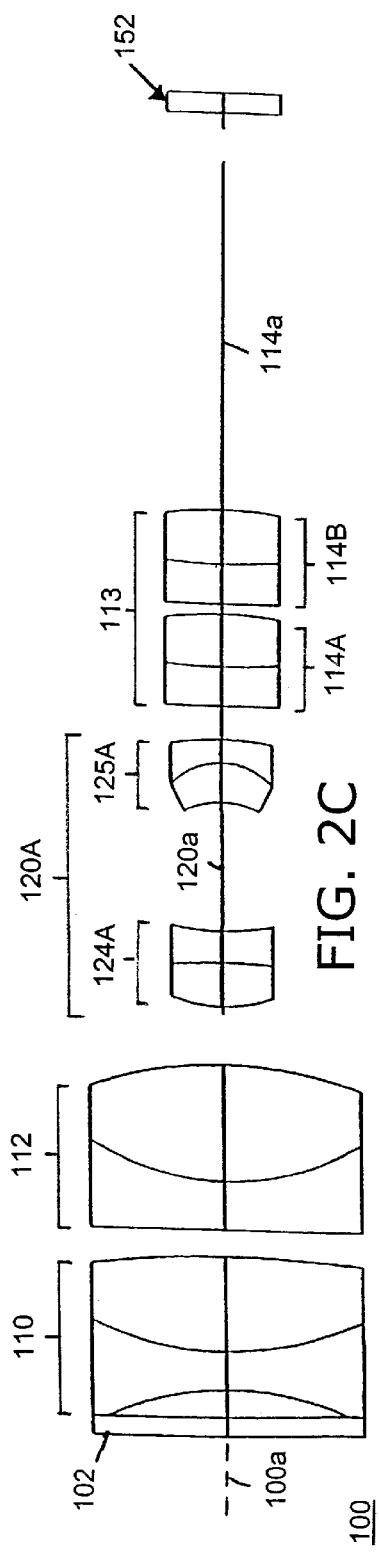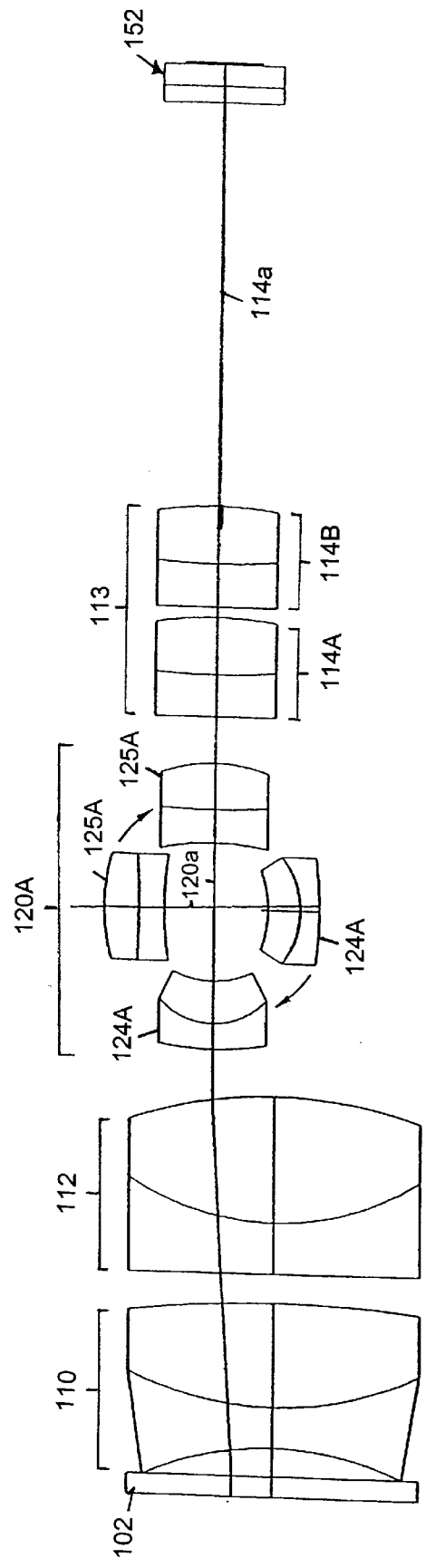

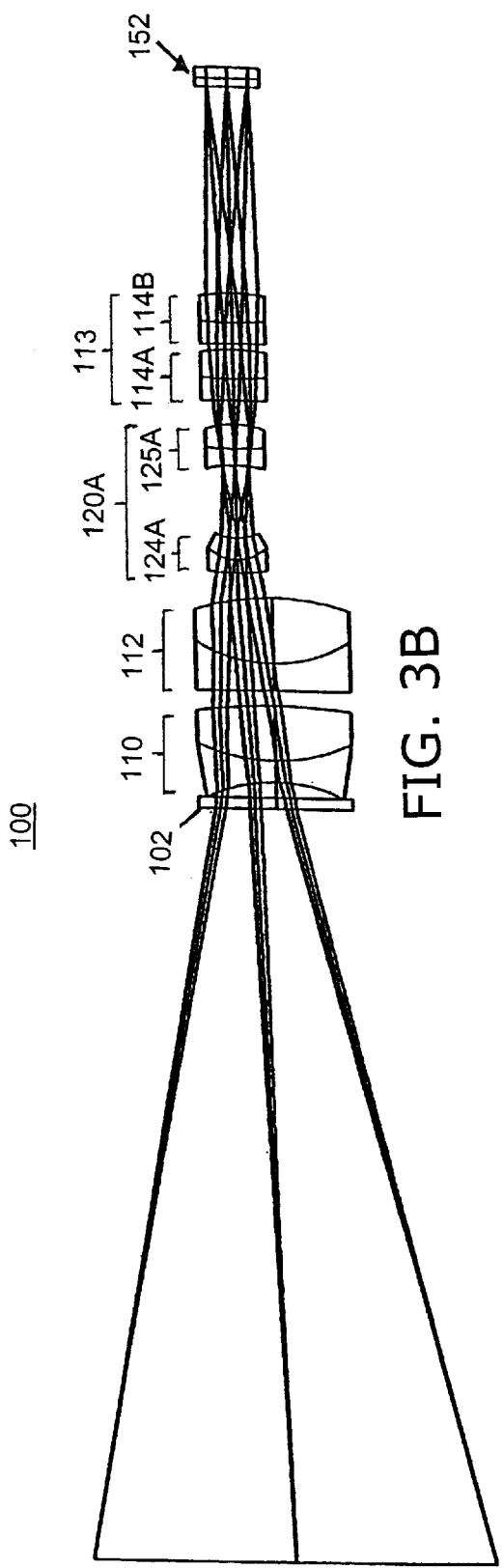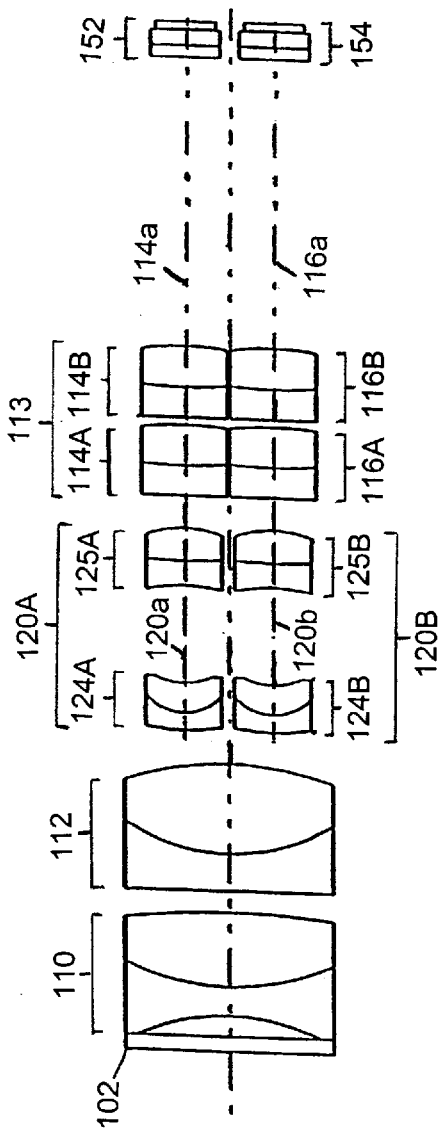
FIG. 3B
FIG. 3C

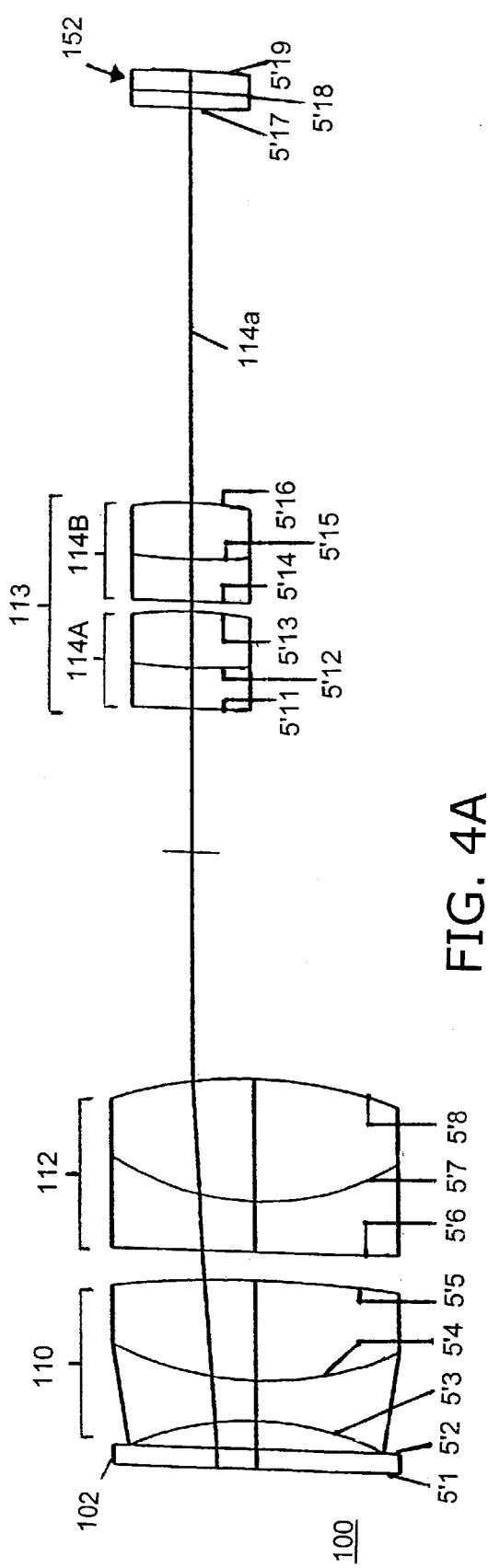
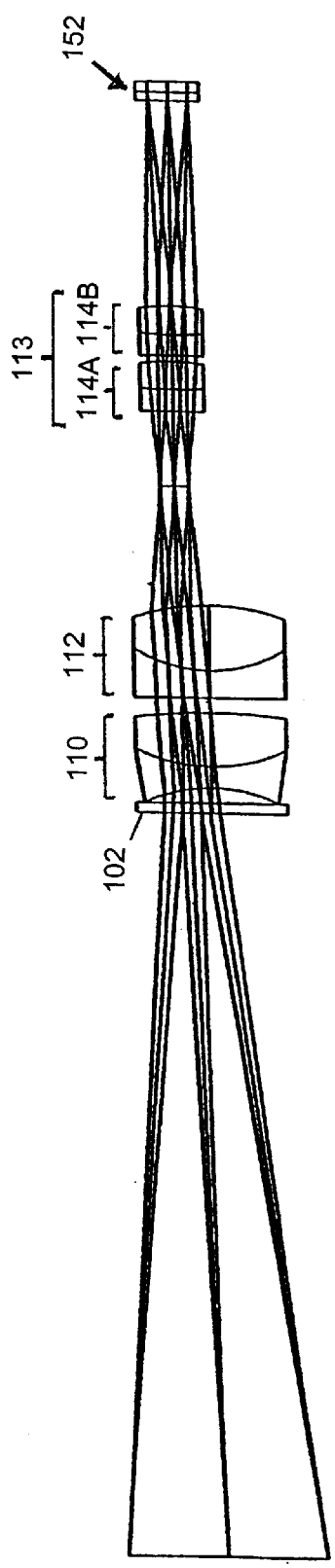
FIG. 4A
FIG. 4B

GENERAL LENS DATA:

| | | |
|---|---|---|
| Surfaces | : | 26 |
| Stop | : | 13 |
| System Aperture | : | Float By Stop Size |
| Ray aiming | : | On |
| X Pupil shift | : | 0 |
| Y Pupil shift | : | 0 |
| Z Pupil shift | : | 0 |
| Apodization | : | Uniform, factor = 0.000000 |
| Eff. Focal Len. | : | 8.74912 (in air) |
| Eff. Focal Len. | : | 8.74912 (in image space) |
| Total Track | : | 69.9339 |
| Image Space F/# | : | 8.10197 |
| Para. Wrkng F/# | : | 8.29095 |
| Working F/# | : | 8.29511 |
| Obj. Space N.A. | : | 0.00636022 |
| Stop Radius | : | 1.1 |
| Parax. Ima. Hgt. | : | 1.8961 |
| Parax. Mag. | : | -0.105339 |
| Entr. Pup. Dia | : | 1.07988 |
| Entr. Pup. Pos. | : | 14.8912 |
| Exit Pupil Dia. | : | 5.15074 |
| Exit Pupil Pos. | : | -42.5646 |
| Field Type | : | Object height in Millimeters |
| Maximum Field | : | 18 |
| Primary Wave | : | 0.587600 |
| Lens Units | : | Millimeters |
| Angular Mag. | : | 0.209655 |

Fields : 3
Field Type: Object height in Millimeters

| # | X-Value | Y-Value | Weight |
|---|---|---|---|
| 1 | 0.000000 | 0.000000 | 1.000000 |
| 2 | 0.000000 | 18.000000 | 1.000000 |
| 3 | 0.000000 | -18.000000 | 1.000000 |

Vignetting Factors

| # | VDX | VDY | VCX | VCY |
|---|---|---|---|---|
| 1 | 0.000000 | 0.000000 | 0.000000 | 0.000000 |
| 2 | 0.000000 | 0.000000 | 0.000000 | 0.000000 |
| 3 | 0.000000 | 0.000000 | 0.000000 | 0.000000 |

Wavelengths : 3
Units: Microns

| # | Value | Weight |
|---|---|---|
| 1 | 0.587600 | 1.000000 |
| 2 | 0.486100 | 1.000000 |
| 3 | 0.656300 | 1.000000 |

FIG. 5A

SURFACE DATA SUMMARY:

| Surf(s) | Type | Radius | Thickness | Glass | Diameter | Conic |
|---|---|---|---|---|---|---|
| OBJ | STANDARD | Infinity | 70 | | 36 | 0 |
| 1 | STANDARD | Infinity | 1 | SAPPHIRE | 13.5 | 0 |
| 2 | STANDARD | Infinity | 1.39394 | | 13.5 | 0 |
| 3 | STANDARD | -14 | 2 | BALF4 | 12 | 0 |
| 4 | STANDARD | 16 | 5 | F2 | 13.5 | 0 |
| 5 | STANDARD | -63.3 | 1.4 | | 13.5 | 0 |
| 6 | STANDARD | Infinity | 2.5 | F2 | 13.5 | 0 |
| 7 | STANDARD | 12.7 | 6 | BALF4 | 13.5 | 0 |
| 8 | STANDARD | -20.1 | 2.2 | | 13.5 | 0 |
| 9 | COORDBRK | --------- | 0 | | 0 | -------- |
| 10 | STANDARD | 14.1 | 1.2 | SSKN5 | 5 | 0 |
| 11 | STANDARD | 3.6 | 2 | SF5 | 5 | 0 |
| 12 | STANDARD | 4 | 6.53 | | 3.7 | 0 |
| STO | STANDARD | Infinity | 0 | | 2.2 | 0 |
| 14 | STANDARD | -12.2 | 1.6 | SF5 | 5 | 0 |
| 15 | STANDARD | 33 | 2.2 | SSKN5 | 5 | 0 |
| 16 | STANDARD | -7.14 | 2.2 | | 5 | 0 |
| 17 | STANDARD | Infinity | 2 | BASF2 | 5.6 | 0 |
| 18 | STANDARD | 26.65 | 2.7 | BK7 | 5.6 | 0 |
| 19 | STANDARD | -18.11 | 0.5 | | 5.6 | 0 |
| 20 | STANDARD | Infinity | 2 | BASEF2 | 5.6 | 0 |
| 21 | STANDARD | 26.65 | 2.7 | BK7 | 5.6 | 0 |
| 22 | STANDARD | -18.11 | 20.9 | | 5.6 | 0 |
| 23 | STANDARD | Infinity | 0.81 | BALF5 | 5.6 | 0 |
| 24 | STANDARD | Infinity | 1 | K50 | 5.6 | 0 |
| 25 | STANDARD | Infinity | 0.1 | | 5.6 | 0 |

FIG. 5B

GENERAL LENS DATA:

| | | |
|---|---|---|
| Surfaces | : | 20 |
| Stop | : | 10 |
| System Aperture | : | Float By Stop Size |
| Ray aiming | : | On |
|    X Pupil shift | : | 0 |
|    Y Pupil shift | : | 0 |
|    Z Pupil shift | : | 0 |
| Apodization | : | Uniform, factor = 0.000000 |
| Eff. Focal Len. | : | 16.3991 (in air) |
| Eff. Focal Len. | : | 16.3991 (in image space) |
| Total Track | : | 68.9339 |
| Image Space F/# | : | 8.20185 |
| Para. Wrkng F/# | : | 8.8074 |
| Working F/# | : | 8.75226 |
| Obj. Space N.A. | : | 0.011609 |
| Stop Radius | : | 1.28 |
| Parax. Ima. Hgt. | : | 1.83856 |
| Parax. Mag. | : | -0.204284 |
| Entr. Pup. Dia | : | 1.99944 |
| Entr. Pup. Pos. | : | 16.1104 |
| Exit Pupil Dia. | : | 5.62011 |
| Exit Pupil Pos. | : | -49.3129 |
| Field Type | : | Object height in Millimeters |
| Maximum Field | : | 9 |
| Primary Wave | : | 0.587600 |
| Lens Units | : | Millimeters |
| Angular Mag. | : | 0.355766 |

Fields : 3
Field Type: Object height in Millimeters

| # | X-Value | Y-Value | Weight |
|---|---|---|---|
| 1 | 0.000000 | 0.000000 | 1.000000 |
| 2 | 0.000000 | 9.000000 | 1.000000 |
| 3 | 0.000000 | -9.000000 | 1.000000 |

Vignetting Factors

| # | VDX | VDY | VCX | VCY |
|---|---|---|---|---|
| 1 | 0.000000 | 0.000000 | 0.000000 | 0.000000 |
| 2 | 0.000000 | 0.000000 | 0.000000 | 0.000000 |
| 3 | 0.000000 | 0.000000 | 0.000000 | 0.000000 |

Wavelengths : 3
Units: Microns

| # | Value | Weight |
|---|---|---|
| 1 | 0.587600 | 1.000000 |
| 2 | 0.486100 | 1.000000 |
| 3 | 0.656300 | 1.000000 |

FIG. 6A

Table B2

SURFACE DATA SUMMARY:

| Surf(s) | Type | Radius | Thickness | Glass | Diameter | Conic |
|---|---|---|---|---|---|---|
| OBJ | STANDARD | Infinity | 70 | | 18 | 0 |
| 1 | STANDARD | Infinity | 1 | SAPPHIRE | 13.5 | 0 |
| 2 | STANDARD | Infinity | 1.39394 | | 13.5 | 0 |
| 3 | STANDARD | -14 | 2 | BALF4 | 12 | 0 |
| 4 | STANDARD | 16 | 5 | F2 | 13.5 | 0 |
| 5 | STANDARD | -63.3 | 1.4 | | 13.5 | 0 |
| 6 | STANDARD | Infinity | 2.5 | F2 | 13.5 | 0 |
| 7 | STANDARD | 12.7 | 6 | BALF4 | 13.5 | 0 |
| 8 | STANDARD | -20.1 | 2.2 | | 13.5 | 0 |
| 9 | COORDBRK | --------- | 8.73 | | 0 | -------- |
| STO | STANDARD | Infinity | 7 | | 2.56 | 0 |
| 11 | STANDARD | Infinity | 2 | BASF2 | 5.6 | 0 |
| 12 | STANDARD | 26.65 | 2.7 | BK7 | 5.6 | 0 |
| 13 | STANDARD | -18.11 | 0.5 | | 5.6 | 0 |
| 14 | STANDARD | Infinity | 2 | BASF2 | 5.6 | 0 |
| 15 | STANDARD | 26.65 | 2.7 | BK7 | 5.6 | 0 |
| 16 | STANDARD | -18.11 | 19.9 | | 5.6 | 0 |
| 17 | STANDARD | Infinity | 0.81 | BALF5 | 5.6 | 0 |
| 18 | STANDARD | Infinity | 1 | K50 | 5.6 | 0 |
| 19 | STANDARD | Infinity | 0.1 | | 5.6 | 0 |
| IMA | STANDARD | Infinity | 0 | | 3.723724 | 0 |

FIG. 6B

MULTIPLE MAGNIFICATION STEREO VIDEO TELESCOPE OBJECTIVE LENS SYSTEM

CROSS-REFERENCE TO RELATED APPLICATIONS

This application is related to and takes priority from U.S. Patent and Trademark Office Provisional Application Ser. No. 60/087,000 filed May 28, 1998, which is incorporated herein by reference.

BACKGROUND OF THE INVENTION

This invention relates generally to optical lens systems, and, more particularly, relates to stereoscopic objective lens designs adapted for use in stereo video telescopes.

Medical endoscopes are a form of telescope which is widely utilized to view internal regions of the human body during diagnostic, surgical, and other medical procedures. Endoscopes typically include a long, thin, rigid or semi-rigid optical cylinder affixed to a viewing mechanism. The cylinder is sufficiently narrow to be inserted through a small opening in the body, which may be natural or surgical. When the endoscope is inserted and positioned for use, an image of the object being viewed is formed at an inserted end of the endoscope by an objective lens. The image passes through a series of relay lenses down the cylinder to an eye lens or video camera at a viewing end of the endoscope.

In recent years, researchers have attempted to improve the imaging available through endoscopic devices by developing stereoscopic video endoscopes. These endoscopes present an apparently three-dimensional image on a video monitor. The stereoscopic effect is created by producing two optical images—a left image and a right image—through the endoscope. The left and right optical images are presented by the endoscope to left and right image sensors, which may be charge-coupled device (CCD) cameras or other image sensing devices. The sensing devices convert the left and right optical images into left and right video images which are then presented as alternating left/right images on a monitor, at a switching rate higher than the flicker-sensing limit of the human eye, so that observed images appear flicker-free.

The images are alternately switched from a left-hand polarization mode to a right-hand polarization mode, such that, for example, the left image has a left-hand polarization and the right image has a right-hand polarization. In accord with this example, the observer wears polarized glasses in which the left lens has the left-hand polarization and the right lens has the right-hand polarization. Thus, the left eye sees only images from the left channel of the endoscope system and the right eye sees only images from the right channel, resulting in stereoscopic viewing.

The following United States and foreign patents disclose examples of stereo endoscopes, some of which utilize video imaging and display elements:

U.S. Pat. No. 4,061,135
U.S. Pat. No. 4,615,332
U.S. Pat. No. 4,651,201
U.S. Pat. No. 4,862,873
U.S. Pat. No. 4,873,572
U.S. Pat. No. 4,895,431
U.S. Pat. No. 5,122,650
U.S. Pat. No. 5,191,203
U.S. Pat. No. 5,673,147
EP Patent No. 211,783

In particular, U.S. Pat. No. 4,061,135 discloses a binocular endoscope in which images are transmitted from the viewed object to the viewing station through an optical system utilizing a dove prism and mechanical linkage to compensate for rotation effects.

U.S. Pat. No. 4,615,332 discloses a binocular endoscope having flexible light guides and binocular eyepieces.

U.S. Pat. No. 4,651,201 discloses a stereoscopic video endoscope including two image guides and an illumination light guide. The image guides are optically coupled to a stereoscopic viewer for three dimensional viewing. The viewer includes couplings for attaching miniature video camera that can be connected to a head mounted stereoscopic video display.

U.S. Pat. No. 4,862,873 discloses a stereo endoscope having two light guides for carrying images of an object an electro-optical imaging assembly. A lens system directs light from the object to the objective end of the light guides. Illuminating light is transmitted to the object from the opposite end of one light guide, thereby illuminating the object. Simultaneously, the image transmitted through the other optical guide is conducted to the imaging assembly.

U.S. Pat. No. 4,873,572 discloses a stereo endoscope having a CCD camera module and two image-forming lens systems that form two object images. The object images are integrated and directed to the CCD camera to provide a stereoscopic output. The lens systems include red, green, and blue color filters disposed at the camera imaging surface.

U.S. Pat. No. 4,895,431 discloses an endoscope apparatus that generates a three-dimensional image of an object from overlapping images recorded by a camera. The endoscope includes an insertion module and a movable end section capable of being deflected through an angle. A first image is recorded with the end section positioned at a first angle. A second image, partially overlapping the first image, is recorded after moving the end section to a second angle. The relative position of the movable end section is detected by an encoder that generates position signals for input to a microprocessor, which utilizes the position signals to generate a three-dimensional image of the object.

U.S. Pat. No. 5,122,650 discloses a stereo video endoscope objective lens system using six doublet lenses to generate pixel mapped left-right images for stereo viewing.

U.S. Pat. No. 5,191,203 discloses a stereo video endoscope objective lens system using lenses having a graded index of refraction to generate pixel mapped left-right images for stereo viewing.

U.S. Pat. No. 5,673,147 discloses a stereo video endoscope objective lens system which uses ball lenses for the left and right stereo lens pair.

European Patent No. 211,783 discloses a stereo video endoscope in which two light pipes deliver two images of the same object. These images are presented by a binocular device to the user's eyes to show a three dimensional image of the target. The apparatus includes two television cameras and video recorders for recording the images. The recorded images can be displayed on separate screens and viewed by a binocular viewing system.

Most conventional stereo endoscopes, however, share a number of deficiencies associated with their objective lens systems. These problems include a bulky and unwieldy configuration; high cost and complexity of fabricating the objective lens system; and the less than optimal optical performance afforded by conventional objective lens systems.

An additional problem associated with conventional stereo video endoscope objectives involves the requirement that all portions of each left/right image be mapped to within a fraction of a video pixel to each other. This pixel mapping condition is a significant optical design constraint, because the object-to-image ray paths through the lens system are quite different for the left and right image points associated with a common object point.

A further problem is the general characteristic of conventional endoscopes that the magnification is fixed for each such instrument. The present invention is directed to the latter problem.

Accordingly, it is a general object of the present invention to provide improved stereo telescope objective lens systems that selectively provides multiple magnifications.

A more specific object is to provide an improved stereo telescope objective lens system having optical elements that may be selectively placed in the optical train to provide different magnifications.

The above and other objects and advantages of this invention will become more readily apparent when the following description is read in conjunction with the accompanying drawings.

SUMMARY OF THE INVENTION

The foregoing objects are attained by the invention, which provides an improved stereo objective lens system for video imaging for various applications.

One aspect of the invention includes two full-diameter (D) doublets disposed along an optical axis, and a left/right stereo lens pair. A rotatable dual telescope, including two Galilean telescopes, is disposed between the full diameter doublets and the left/right stereo lens pair. The stereo lens pair includes a set of two pairs of doublet lenses.

The full-diameter doublets substantially collimate object points, i.e., image them substantially to infinity. The Galilean telescopes preferably each include a pair of doublets positioned along an optical axis, in a rotatable assembly which permits selectively positioning of the Galilean telescopes of their axes (in a magnifying orientation or a reducing orientation or neither). The stereo lens pair is disposed to collect light from the second doublet, if the Galilean telescope is out of the optical train, or from the Galilean telescope if it is in the optical train, with the optical axis of each lens being substantially parallel, and offset from the optical axis of the doublets.

The doublets and the stereo lens pair cooperate so that the doublets present equal angle light ray pairs from symmetrically disposed object points to the lenses of the stereo lens pair. The left and right stereo lenses generate left and right images respectively, at an image plane, where corresponding portions of those images are mapped to within a selected distance of each other.

In another aspect of the invention, the large collimator doublets provide accurate object/image mapping onto the final stereo image pair. In this design, the larger, and hence easier to fabricate doublets carry the corrective burden, so that the smaller, more difficult to manufacture lenses can be made a simple as possible.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWING

For a fuller understanding of the nature and objects of the invention, reference should be made to the following detailed description and the accompanying drawings, in which:

FIGS. 2A–2C is an optical schematic diagram of a stereo objective lens system in accordance with the invention, in "wide angle" mode, "normal" mode and "telephoto" mode, respectively;

FIG. 2D is an optical schematic diagram of an alternative embodiment of the invention;

FIG. 3B is an optical schematic diagram depicting the objective lens system of FIG. 2D in wide angle mode, showing light rays transmitted through the system;

FIG. 3C is an optical schematic diagram depicting the objective lens system of FIG. 2D in wide angle mode, identifying optical surfaces;

FIG. 4A is an optical schematic layout of the embodiment of FIG. 2D in normal angle mode;

FIG. 4B is an optical schematic diagram depicting the objective lens system of FIG. 2D in normal mode, showing light rays transmitted through the system;

FIGS. 5A and 5B set forth Tables A1 and B1 respectively, which define exemplary lenses for the embodiment of FIG. 2D in wide angle mode;

FIGS. 6A and 6B set forth Tables A2 and B2 respectfully, which define exemplary lenses for the embodiment of FIG. 2D in narrow mode;

In the various figures, corresponding elements are identified with the same reference designations.

DESCRIPTION OF ILLUSTRATED EMBODIMENTS

Figure 1:
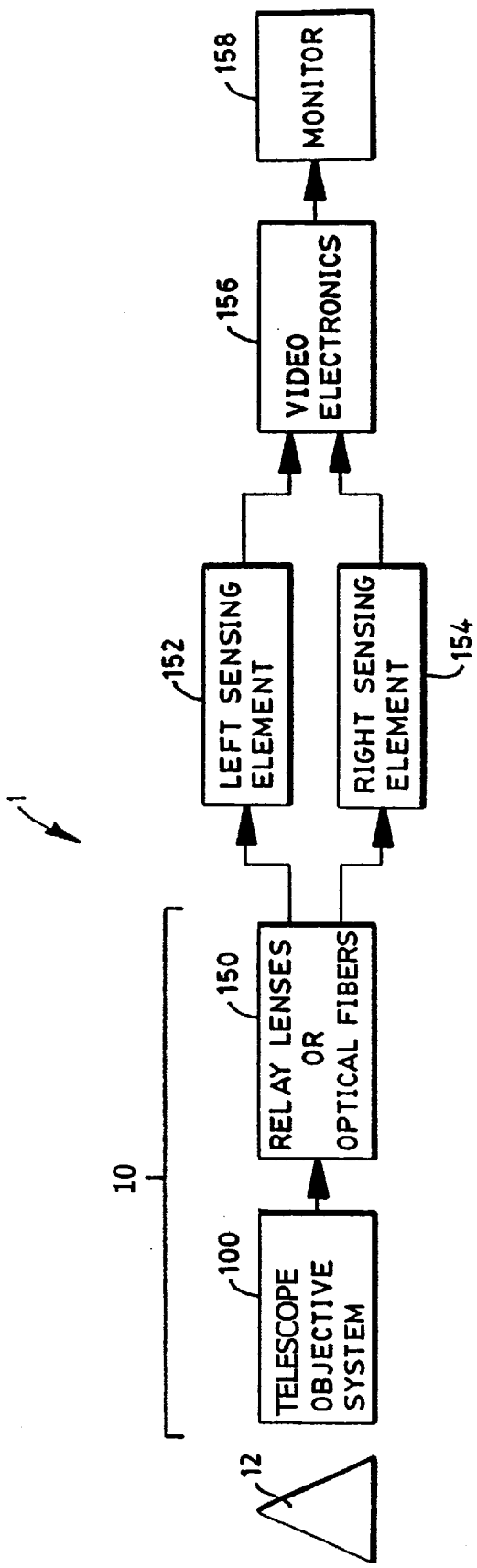
FIG. 1 is a schematic diagram depicting a stereo video endoscope utilizing an objective lens system constructed in accordance with the invention.

FIG. 1 depicts the invention, a telescope objective system 100, utilized in a stereo video optical system 1 for generating stereoscopic images of an object 12. The system 1 principally includes a stereoscopic telescope 10 containing objective system 100; sensing modules 152, 154; switching module 156; and a monitor 158. In addition to objective lens system 100, the telescope 10 includes conventional relay lenses or optical fibers 150 for transmitting light collected by the endoscope objective system 100 to light sensing modules 152, 154.

The telescope objective system 100 generates left and right optical images of the object 12 that are processed by sensing elements 152, 154 and video switching module 156 in a known manner to display an apparently three-dimensional image of the object 12 on video monitor 158.

The stereoscopic effect is created by producing two optical images—a left image and a right image—through the telescope objective system 100. The left and right optical images generated by the objective system 100 are presented by the relay lens or optical fiber system 150 to left and right image sensors 152, 154, which can be conventional charge-coupled device (CCD) cameras or other image sensing devices. The CCD elements operate in a known manner to convert the light collected by the objective system 100, and transmitted by the relay lenses or optical fibers 150, into electrical signals representative of the left and right optical images of the object 12.

Conventional video switching circuitry 156 transmits the electronic signals representative of left and right video images as alternating left-right images on the monitor 158. In accord with known video practice, these alternating images are presented at a switching rate higher than the flicker-sensing limit of the human eye, so that observed images appear flicker-free.

Moreover, the images can be alternately switched from a left-hand polarization mode to a right-hand polarization mode, such that, for example, the left image has a left-hand polarization and the right image has a right-hand polarization. The observer wears polarized glasses in which the left lens has the left-hand polarization and the right lens has the right-hand polarization. Thus, when the observer views the monitor 158, the left eye sees only images from the left channel of the endoscope system and the right eye sees only images from the right channel, resulting in stereoscopic viewing. Video switching and display equipment of this type is commercially available from Stereographics, Inc. of San Rafael, Calif.; and from Tektronix Corp., of Beaverton, Oreg.

The accuracy and quality of the image displayed on monitor 158 is controlled by the performance of the telescope objective system 100, which is the subject of the present invention.

FIGS. 2A–2C and 2D respectively depict alternate forms of an objective lens system 100 constructed in accordance with the invention.

The objective systems 100 of FIGS. 2A–2C and 2D include a window 102 followed by a first doublet 110 and a second doublet 112 positioned in sequence along and centered about a common system axis 100a, followed by a stereo lens set 113. Both of the first doublets have circular cross sections with a diameter D1. The stereo lens set 113 includes two pairs doublets 114A/114B, 116A/116B, each having a circular cross-section with diameter D2, extending along an associated one of lens axes 114a and 116a which are parallel to, and spaced apart by D2 from, the system axis 100a. The two doublets 110, 112 cooperate to collimate object points, i.e., image them to infinity. A CCD detector element 152, 154 follows each of the doublet pairs 114, 116.

A rotatable telescope is positioned between the doublet 112 and stereo lens set 113. The dual telescope includes a first Galilean telescope 120A (including doublets 124A and 125A extending along an optical axis 120a) associated with the axis 114a and second Galilean telescope 120B (including doublets 124B and 125B extending along an optical axis 120b) associated with the axis 116a. Galilean telescope 120A is selectively rotatable about an axis perpendicular to the axis 114a so that (1) its optical axis 120a is aligned with axis 114a (FIGS. 2A, 2C, 2D, 3A, 3B, 3C), with its components doublets 124A, 125A along the system optical axes 100a/114a, or (2) its optical axis 120a is out of line with axis 114a (FIGS. 2B, 2D, 4A, 4B, 4C) with its component doublets 124A, 125A removed completely from the system optical axes 100a, 114a.

Similarly, Galilean telescope 120A is selectively rotatable about an axis perpendicular to the axis 116a so that (1) its optical axis 120b is aligned with axis 114a (FIG. 3C), with its components doublets 124B, 125B along the system optical axes 100a/116a, or (2) its optical axis 120b is out of line with axis 114b (FIGS. 2B, 2D, 4A, 4B, 4C) with its component doublets 124B, 125B removed completely from the system optical axes 100a, 116a. Preferably both Galilean telescopes 120A and 120B of the dual telescope are mounted in a single carriage so that they may be rotated by a user in a single motion. When in the dual telescope is oriented as shown in FIGS. 2B, 4A–4C, the telescope has no effect on the magnification and is termed the "normal" mode. When the telescope is oriented as shown in FIGS. 2A, 3A–3C, the field is increased (with decreased magnification compared with normal mode), and is termed "wide angle" mode. When the telescope is oriented as shown in FIG. 2C, the field is reduced (with increased magnification compared to the normal mode), and is termed the "narrow angle" mode.

Figure 3A:
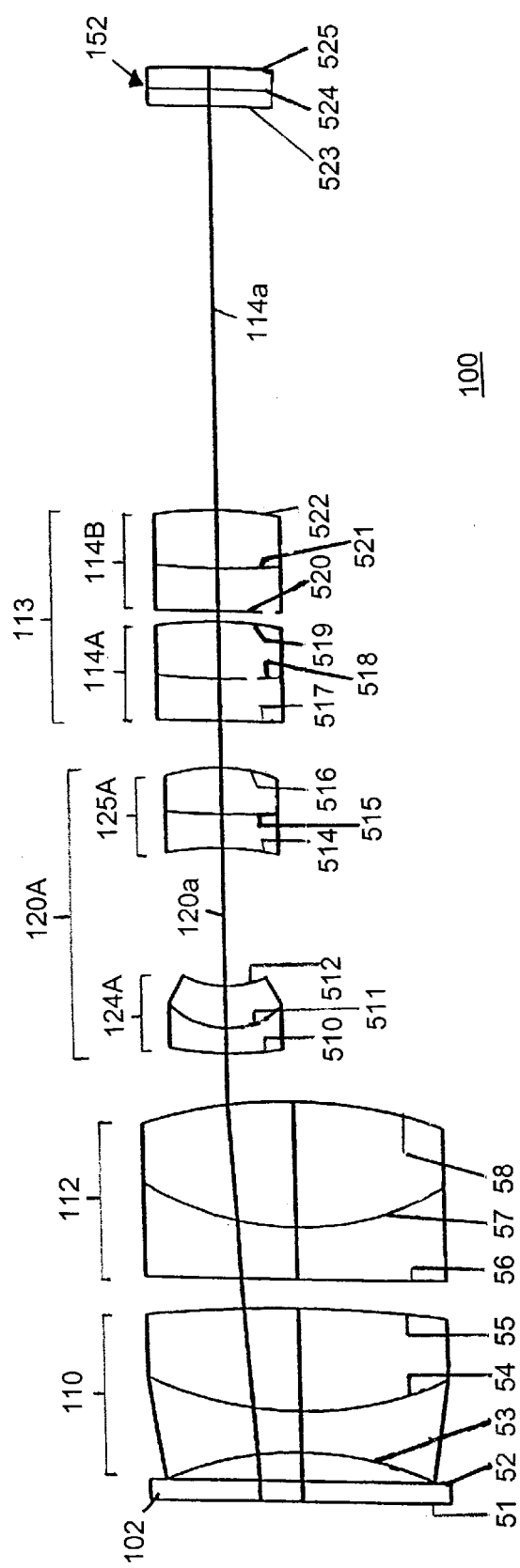
FIG. 3A is an optical schematic layout of the embodiment of FIG. 2D in wide angle mode.
Figure 3D:
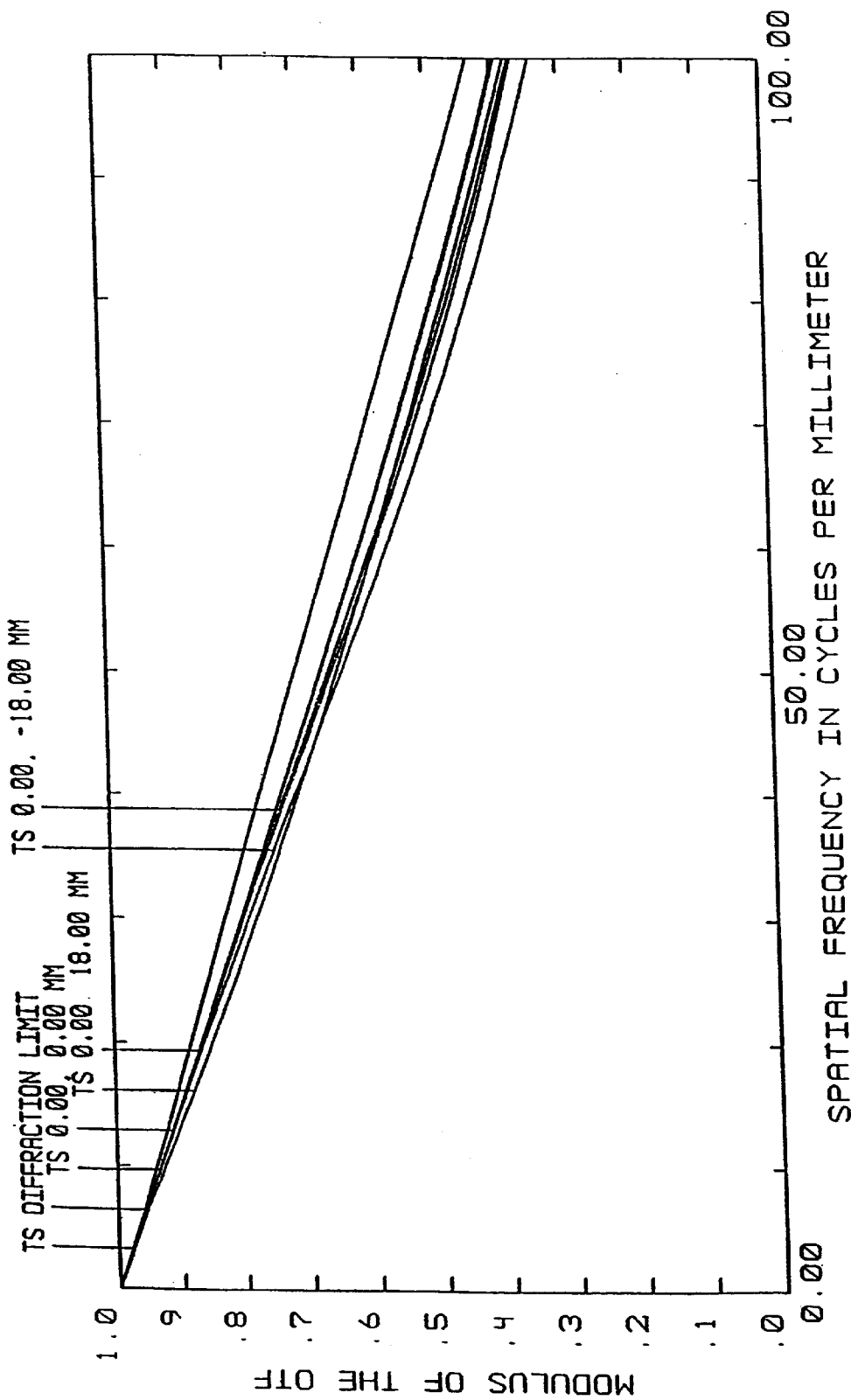
FIG. 3D shows the polychromatic diffraction modulation transfer function for the objective lens system of FIG. 2D in wide angle mode.
Figure 4C:
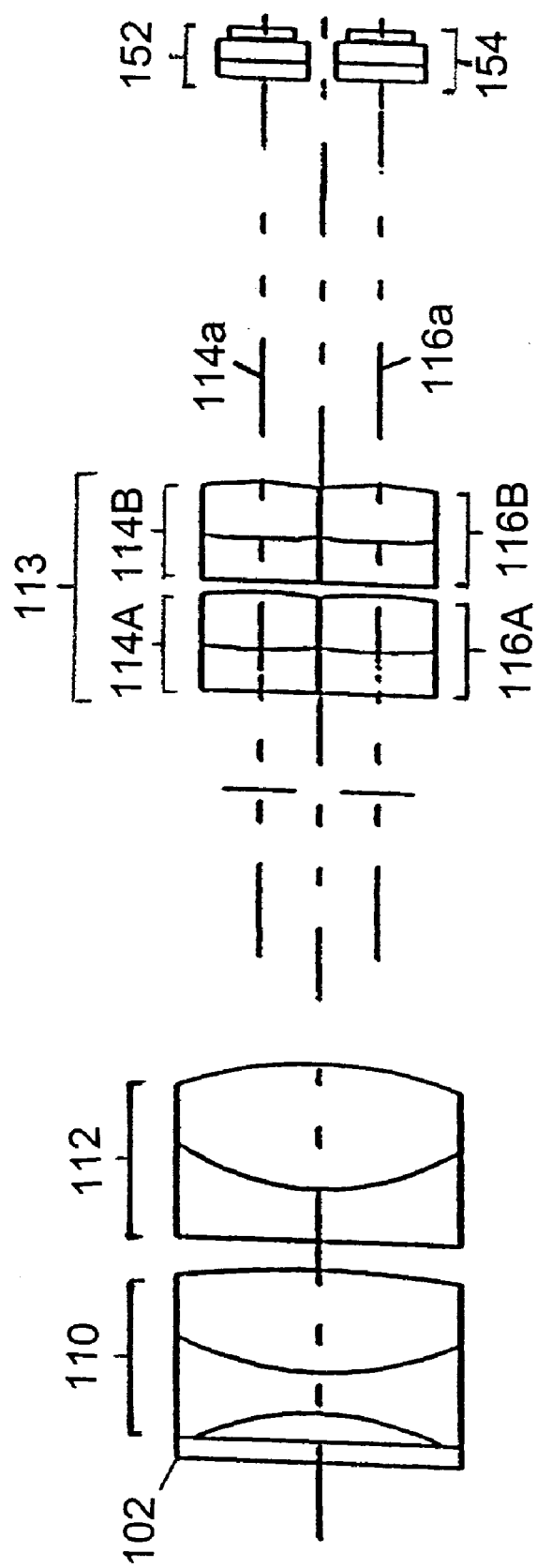
FIG. 4C an optical schematic diagram depicting the objective lens system of FIG. 2D, in normal mode, identifying optical surfaces.
Figure 4D:
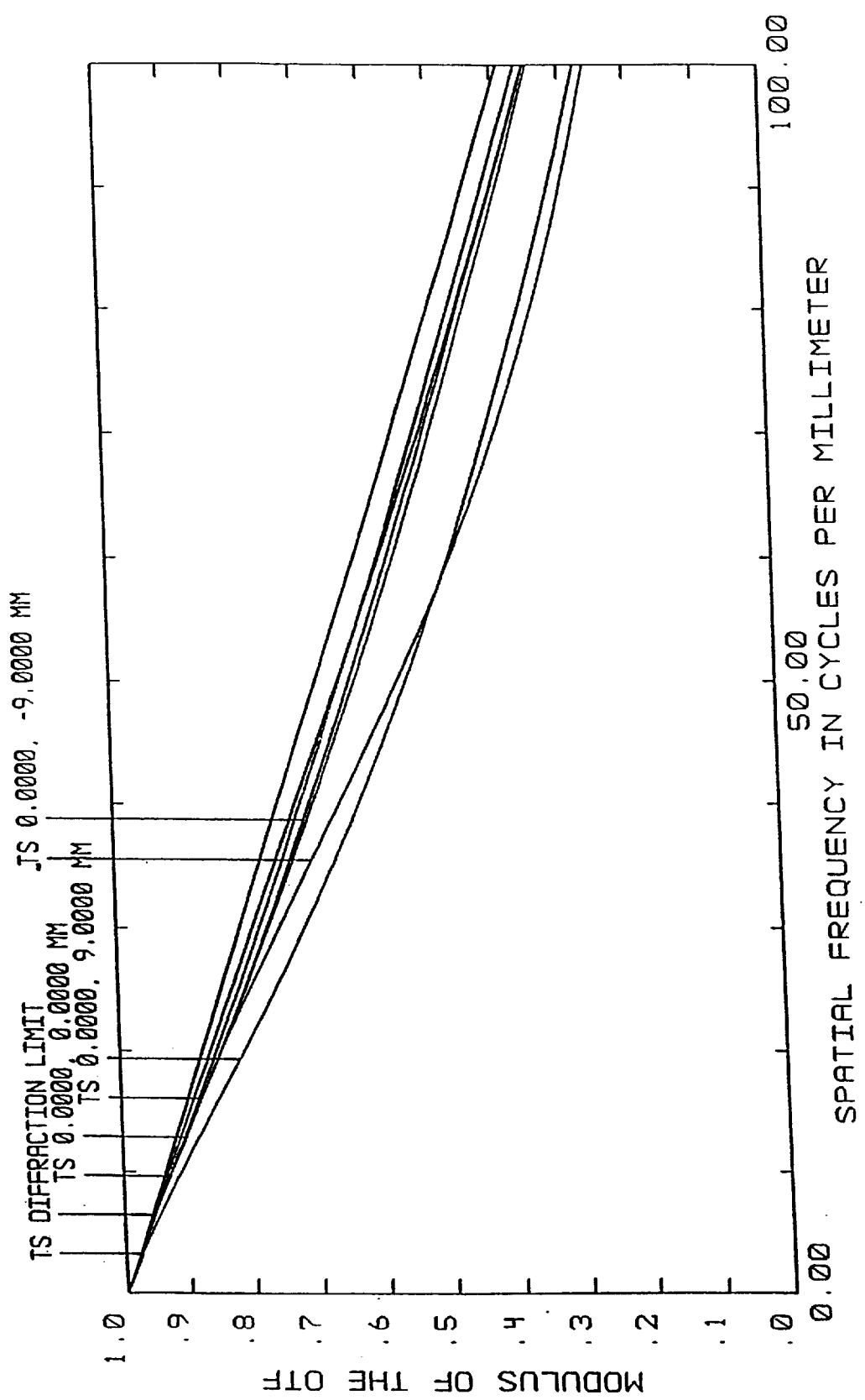
FIG. 4D shows the polychromatic diffraction modulation transfer function for the objective lens system of FIG. 2D in normal mode.

FIGS. 3D and 4D show the polychromatic diffraction modulation transfer function for the embodiment of FIG. 2D, for wide angle mode and normal mode respectively.

Those skilled in the art will appreciate that the lenses of the objective system 100 depicted in FIG. 2D, define a sequence of optical surfaces. Tables A1 (FIG. 5A), A2 (FIG. 5B), B1 (FIG. 5A) and B2 (FIG. 6B) define the exemplary lenses for the embodiment of FIG. 2D. Reference numerals preceded by S (in FIG. 3A) and S' (in FIG. 4A) correspond to the numerals respectively in the "SURFACE" column of Tables A1 and B1. As those skilled in the art will appreciate, surfaces 9 and STO do not correspond to physical surfaces and are indicated in Tables A2 and B2 for convenience of analysis.

In Tables A2 and B2, the numerical values in the "RADIUS", "THICKNESS" and "DIAMETER" columns are set forth in millimeters. The "GLASS" descriptions are standard optical glass characterizations as found in the product catalog of the Schott Glass Company of Germany. The "THICKNESS" column refers to the distance to the next optical surface. The "RADIUS" column refers to the radii of curvature of the respective curved surfaces.

The system 100 is designed so that all parts of each left/right image are mapped to within a selected distance of each other such that stereoscopic image quality is maintained. For video applications, this selected distance is typically a fraction of a video pixel. This is a difficult condition to satisfy, because the objectto-image ray paths through the lens system are quite different for the left and right image points of a common object point. The ray paths shown in FIGS. 3B and 4B demonstrate how differently an object point is imaged through the lens elements for one of the left and right images.

The objective systems 100 depicted in the above figures are able to map all parts of each left/right image to within a fraction of a video pixel to each other, because the large collimator doublets present equal-angle pairs from symmetrically disposed object points to the lenses of the stereo lens set 113. This exact equal-angle solution results in an accurate object/image mapping onto the final stereo image pair.

In the illustrated embodiments, the front full-diameter lenses are essentially a collimator, rendering an object into a virtual image at infinity. This is not essential but rather is a characteristic of the illustrated embodiments.

The collimator provides equal-angle chief rays from symmetrical edges of the field. This equal angle concept, coupled with the symmetry of the system in the left/right channels, insures that the smaller stereo lenses image those field edges at exactly the same positions on the CCD. That is, the right image of the left edge will be at the same position on the left CCD as is the left image of the left edge on the right CCD, and so on. This is an important factor in stress-free 3D viewing.

To obtain such equal-angle chief rays the front lenses have widely separated left-right pupils, so the chief rays of all field bundles are widely separated. As a result, these bundles have non-trivial included angles in object space—i.e. the front lenses are working at some tangible optical speed. In close-up medical use or inspection systems, this optical speed in stereo object space can be considerable, so any aberration of the front lens group will cause a disparity in the chief ray angles in the left-right bundles presented to the stereo lens sets, resulting in left-right image position errors. This stereo mapping error can lead to eyestrain, headaches, and the like, that make stereo visualization difficult.

Objective system 100, as described in Tables A1, A2, B1, and B2, shown in FIG. 2D, achieves accurate object/image mapping with user selectable field magnification depending on the rotational state of the dual Galilean telescope. Tables A1 and A2 in FIGS. 5A and 5B respectively, set forth a detailed description of the embodiment of FIG. 2D in the wide angle mode (FIGS. 3A–3C), and Tables B1 and B2 in FIGS. 6A and 6B, respectively, set forth a detailed description of the embodiment of FIG. 2D in the normal mode (FIGS. 4A–4C).

As indicated in FIG. 1, a telescope constructed using relay lenses 150 or optical fibers or alternatively can employ a conventional CCD array mounted within the same housing as the objective system. The CCD array can include left and right sensing elements 152, 154, disposed to receive the optical images generated at the output of the lenses of stereo lens set 113. The design and construction of CCD elements having more than one photosensitive region in a monolithic package is well known in the art. The electrical signals generated by the CCD array can be conducted from the housing by a conventional conduit. This configuration eliminates the requirement for a relay lens system or optical fibers.

Figure 7B:
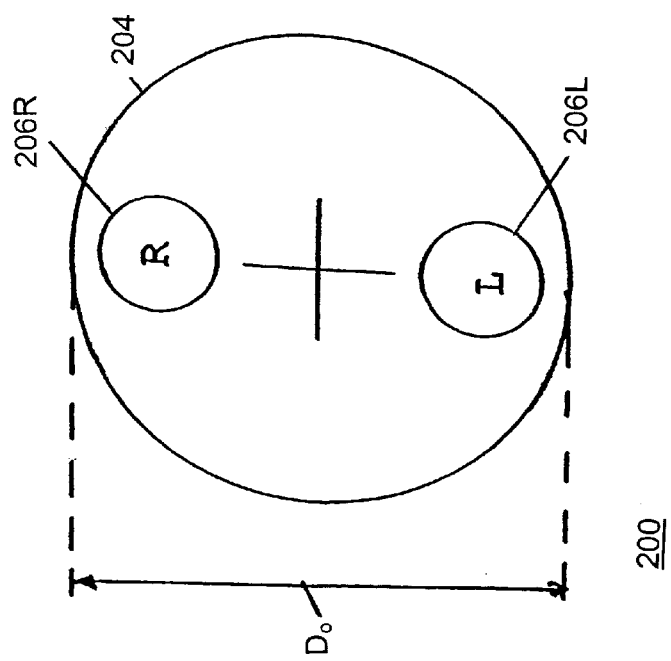
FIG. 7B is an end view of the system of FIG. 7A.
Figure 7A:
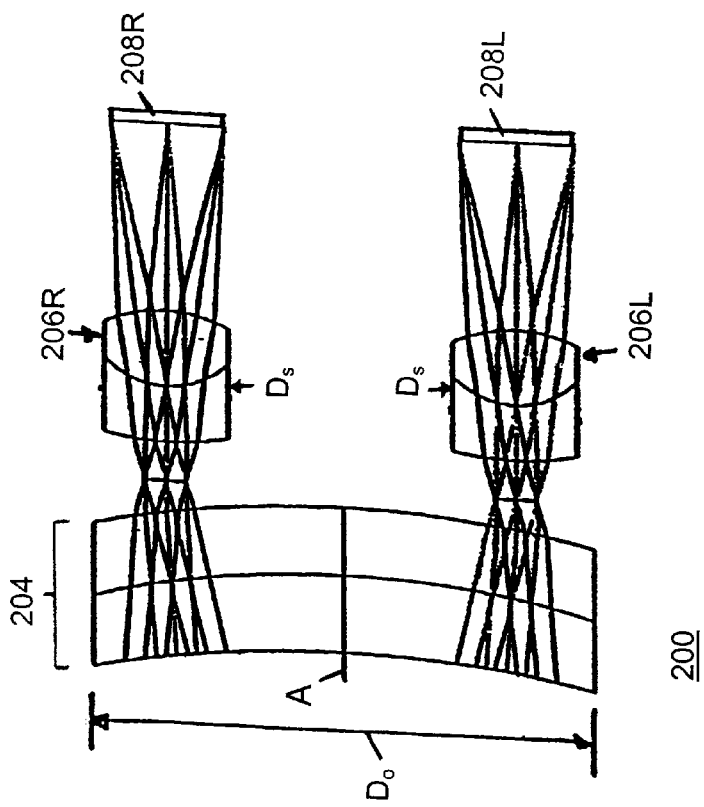
FIG. 7A is an optical schematic diagram of a stereo objective lens system in accordance with another embodiment of the invention, suitable for relatively long object distances.
Figure 8B:
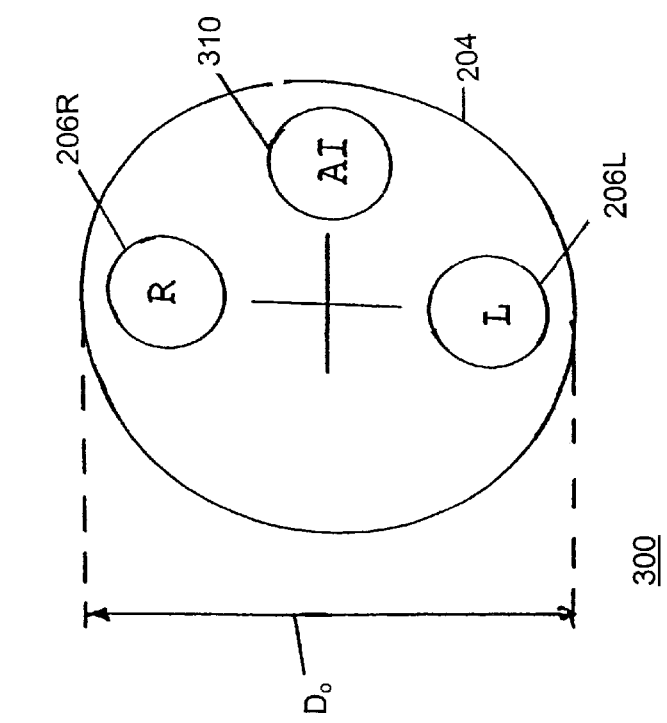
FIG. 8B is an end view of the system of FIG. 8A.

The above described stereo optical systems are particularly well suited for relatively small geometry endoscope systems. However, similar configurations may be used for larger sized systems, such as may be useful for 3-D video teleconferencing or industrial use. By way of example, a system 200 is shown in FIGS. 7A and 7B, which includes a full diameter collimating doublet lens assembly 204, having a relatively large diameter followed by a pair of stereo doublet lenses 206R, 206L, each having a relatively small diameter $D_S$, for the respective right and left channels. The stereo pair is followed by, right and left channel detectors 208R, 208L. In the configuration of FIGS. 7A and 7B, the front full diameter lens assembly 204 is essentially a collimator, rendering an object into a virtual image at infinity. This is not essential, but is the form of the preferred embodiment.

The collimator lens assembly 204 provides equal-angle chief rays from symmetrical edges of the field. This equal angle concept, coupled with the symmetry of the system in the left/right channels, insures that the small stereo lenses image those field edges at exactly the same positions on the CCD detectors 208R and 208L. That is, the left image of the left edge is at the same position on the left CCD 208L, as is the right image of the left edge on the right CCD 208R. This aspect enables stress-free viewing for a user.

The front lenses have widely separated left-right pupils, so that the chief rays of all field bundles are widely separated. As a result, these bundles have nontrivial included angles in object space—i.e. the front lenses are working at some tangible optical speed. In close-up medical use or inspection systems, this optical speed in stereo object space is important since any aberration of the front lens group causes a disparity in the chief ray angles in the left-right bundles presented to the stereo lens sets, resulting in left-right image position errors. This stereo mapping error can cause eyestrain, headaches and the like, that are the problematic for stereo visualization.

In prior art configurations for endoscopes, the front lenses have been designated as "full diameter", while the stereo components have been "half-diameter". In many non-medical applications, however, the stereo components 206R and 206L are considerably less than half the diameter of the front lens assembly 204. This sizing of elements is primarily the result of achieving useful stereo parallax angles in object space. Because large, non-medical systems, especially teleconferencing systems, are designed with long object distances, in the order of a meter, stereoscopy requires a relatively wide stereo baseline. The stereo baseline is established by the separation of the stereo lens pairs 206R, 206L. Accordingly, these lenses are relatively widely separated with respect to the front components 204, compared with the short working distance medical designs, such as those in FIGS. 2A–2C and 2D.

Figure 10B:
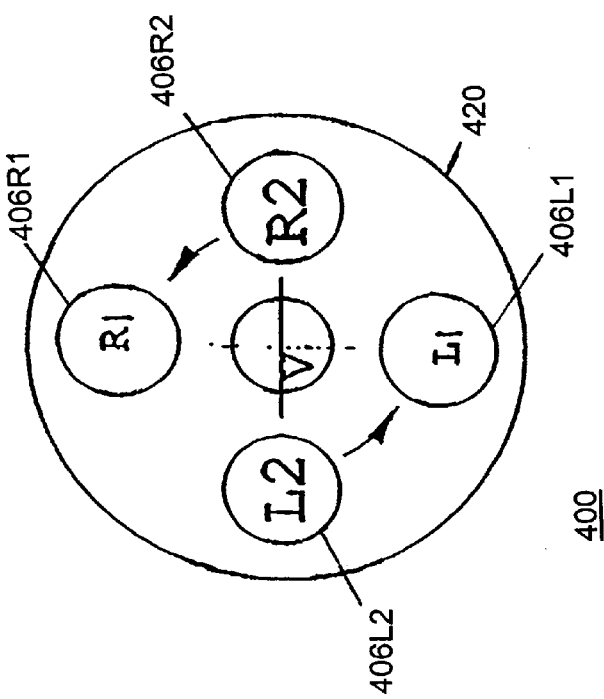
FIGS. 10A and 10B show views of a stereo objective system similar to the stereo objective system as illustrated in FIGS. 7A and 7B respectively.
Figure 10A:
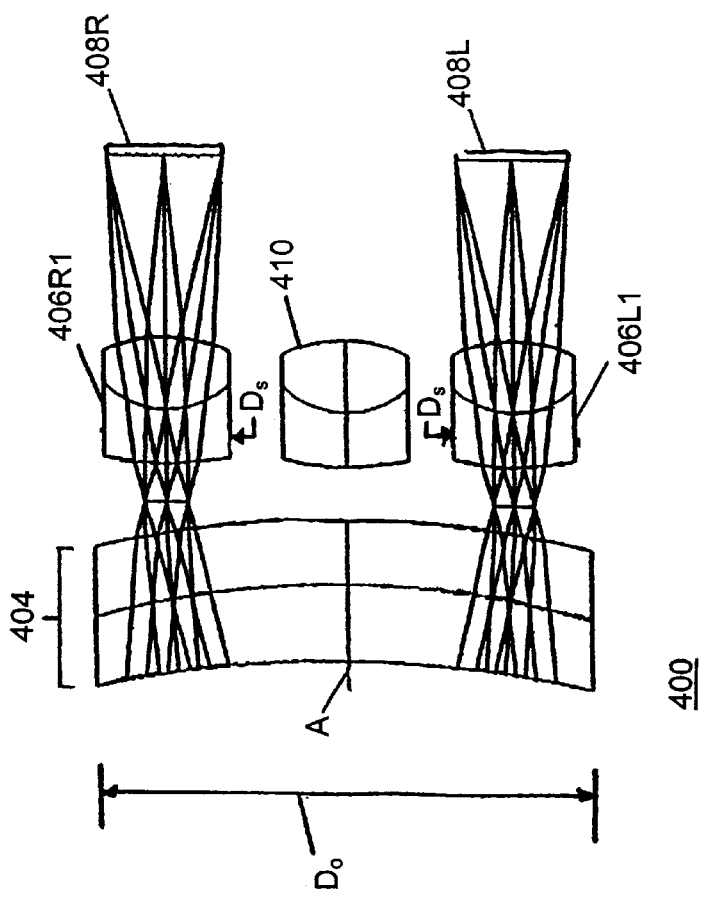

Still another form of the invention is shown in FIGS. 10A and 10B. In those figures, a stereo objective system 400 is shown, which is similar the stereo objective system 200 of FIGS. 7A and 7B, and includes a collimator doublet lens 404 and a first pair of right/left stereo lenses, 406R1, 406L1, and CCD detectors 408R, 408L, and further includes a second right/left stereo lens pair 406R2, 406L2 and an optional third "added information", or "AI", channel lens 410. The lenses 406R1, 406L1, 406R2, 406L2 and 410 are all mounted on a base 420 which is selectively rotatable about the axis A of the collimator doublet lens 404.

In a first state, the base 420 is oriented about axis A (as shown in FIGS. 10A and 10B) so that the optical axes of the first stereo lens pair 406R1, 406L1 are aligned in the same manner as the corresponding lenses in the system of FIGS. 7A and 7B, where those lenses 406R1, 406L1 are in the optical path of the overall system, including collimator doublet lens 404 and earlier elements in the optical train; lenses 406R2 and 406L2 are not in the system optical path in this first state. In a second state (not shown), the base 420 is oriented about axis A so that the optical axes of the second stereo lens pair 406R2, 406L2 are aligned in the manner of the system of FIGS. 7A and 7B, where those lenses 406R2, 406L2 are in the optical path of the overall system, including collimator doublet lens 404, and earlier elements in the optical train; lenses 406R1 and 406L1 are not in the system optical path in this second state. Preferably, lenses 406R1, 406L1 provide a different magnification train lenses 406R2, 406L2, so that switching the orientation of base 420 between the first state and second state provides different magnifications for the optical train of the overall system. This aspect of the invention is useful in a camera, and particularly useful in a digital camera. While shown for two discrete magnifications, in other embodiments, additional stereo lens pairs may be mounted on base 420, permitting addition magnifications to be selectively used.

In one exemplary configuration, the diameters of lenses 406R1, 406L1, 406R2, 406L2, and 410 are approximately one fourth the diameter of lens 404, and the lenses 406R1, 406L1, 406R2, 406L2 and 410 are offset from the axis of lens 404 by approximately one third the diameter of lens 404. Other dimensions may be used in other embodiments.

Figure 9:
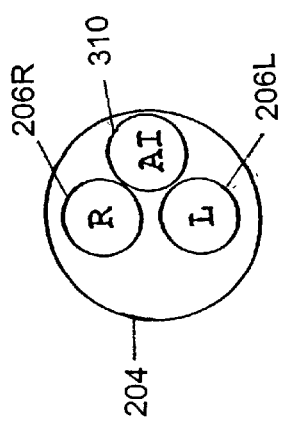
FIG. 9 is an end view of a stereo objective lens system similar to that of FIGS. 8A and 8B, but being a small, closely packed configuration.
Figure 8A:
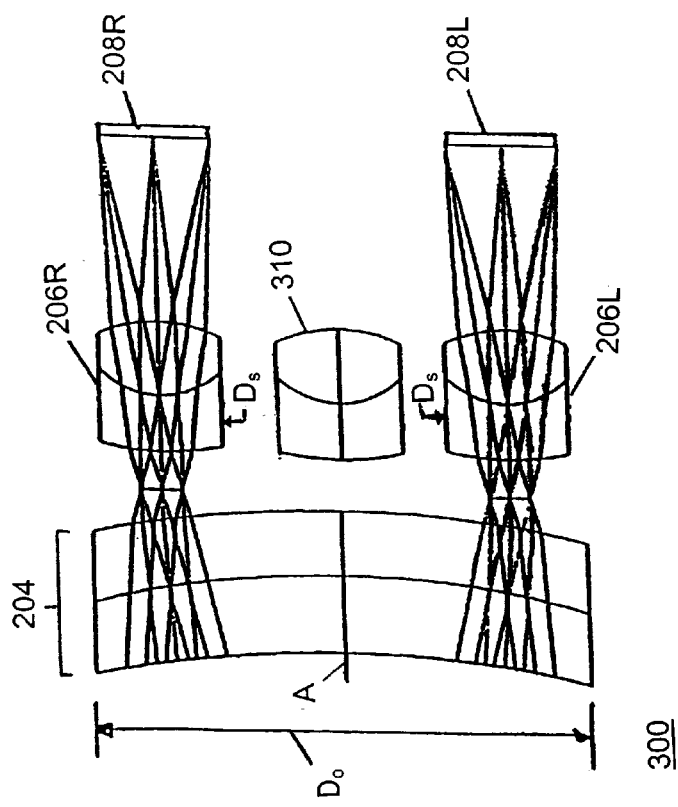
FIG. 8A is an optical schematic diagram of a stereo objective lens system in accordance with another embodiment of the invention, showing a third information channel.

The third channel includes a third channel lens 410. The third channel can be used in many ways—to provide a "viewfinder" for a camera system, to present a "picture-in-picture" display, to provide a 2D image for recording and the like. In addition, with the addition of an external (to the large lens) mirror and/or prism system, the third channel can be steered to view another object. This other object could be another person, in a teleconferencing system "picture-in-picture" (PIP) mode, or an object or a drawing, or just another general scene of interest. The third channel lens 310 need not be the same as the stereo lenses 406R1, 406L1, 406R2, and 406L2. A different object and image format may be chosen to meet specific system requirements. While shown in FIGS. 10A and 10B for large format systems, such as may be useful in cameras, teleconferencing and other large scale industrial applications, the third channel aspect of the invention may be implemented in a closely packed small stereo system, in the same manner as in the system illustrated in FIG. 9.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Having described the invention, what is claimed as new and secured by Letters Patent is:

1. A stereoscopic objective lens system for a stereo video telescope, the objective lens system having elements disposed along an optical path to convert light propagated from an object and received at an objective end of the objective system to pixel-mapped right and left optical images of said object at an image plane end of the objective system, the objective lens system comprising:

A. a first collimator doublet lens disposed along said optical path and proximate to the objective end for collecting light from points on the object, said first collimator doublet lens having a first optical axis, a selected diameter and a selected optical power, B. a second collimator doublet lens for collecting light from said first collimator doublet lens, said second collimator doublet lens being disposed along said optical path and adjacent to said first collimator doublet lens and having a second optical axis substantially collinear with said first optical axis of the first collimator doublet lens, said second collimator doublet lens having a selected diameter and a selected optical power, whereby said first and second collimator doublet lenses cooperate to image the object points substantially to infinity so that light transmitted by the second collimator doublet lens from the object points is substantially collimated, C. a multiple field right/left stereo lens pair assembly including on a base:
  (i). a first right/left stereo lens pair, said first pair including a first pair right stereo lens and a first pair left stereo lens, said first pair right and first pair left stereo lenses being adjacent to said second collimator doublet lens and disposed for collecting light from said second collimator doublet lens, said first pair right stereo lens and said first pair left stereo lens each having a respective optical axis substantially parallel to said second optical axis of the second collimator doublet lens,
  (ii). a second right/left stereo lens pair, said second pair including a second pair right stereo lens and a second pair left stereo lens, said second pair right and second pair left stereo lenses being adjacent to said second collimator doublet lens and disposed for collecting light from said second collimator doublet lens, said second pair right stereo lens and said second pair left stereo lens each having a respective optical axis substantially parallel to said second optical axis of the second collimator doublet lens, wherein the magnifications of said first and second pair right and left stereo lenses are different, wherein said base and said first and second right/left stereo lens pair are rotatable about a pivot axis parallel to said first optical axis to selectively be in a first state wherein:

said optical axes of said first right/left stereo lens pair are each a parallel sub-component part of said optical path, and said first and second collimator doublet lenses and said first right/left stereo lens pair cooperate so that the first and second collimator doublet lenses present equal-angle chief ray pairs from symmetrically disposed object points to the lenses of said first right/left stereo lens pair, and whereby said first pair right lens generates a right image at the image plane, and said first pair left lens generates a left image at the image plane, such that corresponding portions of each right/left image are mapped to within a selected distance of each other, or in a second state wherein said optical axes of said second right/left stereo lens pair are each a parallel sub-component part of said optical path, and said first and second collimator doublet lenses and said second right/left stereo lens pair cooperate so that the first and second collimator doublet lenses present equal-angle chief ray pairs from symmetrically disposed object points to the lenses of said second right/left stereo lens pair, and whereby said second pair right stereo lens generates a right image at the image plane, and said second pair left stereo lens generates a left image at the image plane, such that corresponding portions of each right/left image are mapped to within a selected distance of each other.

2. A lens system according to claim 1 wherein the diameter of said second collimator doublet lens is approximately equal to the diameter of said first collimator doublet lens.

3. A lens system according to claim 2 wherein said right stereo lens is substantially identical to said left stereo lens.

4. A lens system according to claim 3 wherein said right stereo lens and said left stereo lens each have a circular cross-section transverse to the respective optical axes of said right stereo lens and said left stereo lens.

5. A lens system according to claim 3 wherein the diameters of said right stereo lens and said left stereo lens are less than or equal to one-half the diameter of said first and second collimator doublet lenses, and said optical axes of said right stereo lens and said left stereo lens are off-set from said first and second optical axes of said first and second collimator doublet lenses by more than one-fourth the diameter of said first and second collimator doublet lenses.

6. A lens system according to claim 5 wherein said right stereo lens and said left stereo lens each have a circular cross-section transverse to the respective optical axes of said right stereo lens and said left stereo lens.

7. A dual telescope including a first Galilean telescope including two doublets extending along a first axis and a second Galilean telescope including two doublets extending along a second axis, said second Galilean telescope being adjacent to a right/left stereo lens pair, said pair including a right stereo lens and a left stereo lens for generating a right image and a left image, respectively, of an object, said right stereo lens and said left stereo lens each having a respective optical axis, said optical axes of said right/left stereo lens pair each being a parallel sub-component part of an optical path, wherein said first and second Galilean telescopes are each rotatable about a respective pivot axis perpendicular to said optical axes of said right and left stereo lenses to selectively be in a first state wherein:

said first axis is in alignment with said optical axis of said left stereo lens and said second axis is in alignment with said optical axis of said right stereo lens, whereby said doublets of said first and second Galilean telescopes are in said optical path, or in a second state wherein:

said first axis is out of alignment with said optical axis of said left stereo lens and said second axis is out of alignment with said optical axis of said right stereo lens, whereby said doublets of said first and second Galilean telescopes are out of said optical path.

8. A stereoscopic objective lens system for a stereo video telescope, the objective lens system having elements disposed along an optical path to convert light propagated from an object and received at an objective end of the objective system to pixel-mapped left and right optical images at an image plane end of the objective system, the objective lens system comprising:

A. a collimator lens system proximate to the objective end for collecting light propagated from points on the object, said collimator lens system being disposed along said optical path and having a defined optical axis, a selected diameter and a selected optical power, whereby said collimator lens system images the object points substantially to infinity so that light transmitted by said collimator lens system from the object points is substantially collimated, B. a right/left stereo lens pair, said pair including a right stereo lens and a left stereo lens, said right and left stereo lenses being adjacent to said collimator lens system and disposed for collecting light from said collimator lens system, said right stereo lens and said left stereo lens each having a respective optical axis substantially parallel to the optical axis of the collimator lens system, said optical axes of said right/left stereo lens pair each being a parallel sub-component part of said optical path, wherein said collimator lens system and said right/left stereo lens pair cooperate so that the collimator lens system presents equal-angle chief ray pairs from symmetrically disposed object points to the lenses of said right/left stereo lens pair, C. a dual telescope including a first Galilean telescope including two doublets extending along a first axis and a second Galilean telescope including two doublets extending along a second axis, wherein said first and second Galilean telescopes are each rotatable about a respective pivot axis perpendicular to said optical axes of said right and left stereo lenses to selectively be in a first state wherein:

said first axis is in alignment with said optical axis of said left stereo lens and said second axis is in alignment with said optical axis of said right stereo lens, whereby said doublets of said first and second Galilean telescopes are in the optical path of said system, or in a second state wherein said first axis is out of alignment with said optical axis of said left stereo lens and said second axis is out of alignment with said optical axis of said right stereo lens, whereby said doublets of said first and second Galilean telescopes are out of said optical path of said system, whereby said right stereo lens generates a right image at the image plane, and said left stereo lens generates a left image at the image plane, such that corresponding portions of each right/left image are mapped to within a selected distance of each other.

9. A lens system according to claim 8 wherein said collimator lens system comprises:

A. a first collimator doublet lens disposed along said optical path and proximate to the objective end for collecting light from points on the object, said first collimator doublet lens having a first optical axis substantially collinear with said optical axis of said collimator lens system, said first collimator doublet lens having a selected diameter and a selected optical power, B. a second collimator doublet lens for collecting light from said first collimator doublet lens, said second collimator doublet lens being disposed along said optical path and adjacent to said first collimator doublet lens and having a second optical axis substantially collinear with said first optical axis of said first collimator doublet lens, said second collimator doublet lens having a selected diameter and a selected optical power, whereby said first and second collimator doublet lenses cooperate to image the object points substantially to infinity so that light transmitted by the second collimator doublet lens from the object points is substantially collimated; and further wherein the diameter of said second collimator doublet lens is approximately equal to the diameter of said first collimator doublet lens.

10. A lens system according to claim 9 wherein said right stereo lens is substantially identical to said left stereo lens.

11. A lens system according to claim 10 wherein said right stereo lens and said left stereo lens each have a circular cross-section transverse to the respective optical axes of said right stereo lens and said left stereo lens.

12. A lens system according to claim 9 wherein the diameters of said right stereo lens and said left stereo lens are less than or equal to one-half the diameter of said first and second collimator doublet lenses, and said optical axes of said right stereo lens and said left stereo lens are off-set from said first and second optical axes of said first and second collimator doublet lenses by one-fourth the diameter of said first and second collimator doublet lenses.

13. A lens system according to claim 12 wherein said right stereo lens and said left stereo lens each have a circular cross-section transverse to the respective optical axes of said right stereo lens and said left stereo lens.

14. A lens system according to claim 8 wherein first and second Galilean telescopes are mounted in a single carriage whereby said first and second telescopes are rotatable in concert about said pivot axis in response to an applied force.

15. A multiple field stereoscopic objective lens system for a stereo digital camera, the objective lens system having elements disposed along an optical path to convert light propagated from an object and received at an objective end of the objective system to pixel-mapped left and right optical images of said object at an image plane end of the objective system, the objective lens system comprising:

A. a first collimator doublet lens disposed along said optical path and proximate to the objective end for collecting light from points on the object, said first doublet lens having a first optical axis, a selected diameter and a selected optical power, B. a second collimator doublet lens for collecting light from said first collimator doublet lens, said second collimator doublet lens being disposed along said optical path and adjacent to said first collimator doublet lens and having a second optical axis substantially collinear with said first optical axis of the first collimator doublet lens, said second collimator doublet lens having a selected diameter and a selected optical power, whereby said first and second collimator doublet lenses cooperate to image the object points substantially to infinity so that light transmitted by the second collimator doublet lens from the object points is substantially collimated, C. a multiple field left/right stereo lens pair assembly including on a base:
  i. a first right/left stereo lens pair, said first pair including a first pair right stereo lens and a first pair left stereo lens, said first pair right and first pair left stereo lenses being adapted for positioning adjacent to said second collimator doublet lens and disposed for collecting light from said second collimator doublet lens, said first pair right stereo lens and said first pair left stereo lens each having a respective optical axis substantially parallel to said second optical axis of the second collimator doublet lens,
  ii. a second right/left stereo lens pair, said second pair including a second pair right stereo lens and a second pair left stereo lens, said second pair right and second pair left stereo lenses being adapted for positioning adjacent to said second collimator doublet lens and disposed for collecting light from said second collimator doublet lens, said second pair right stereo lens and said second pair left stereo lens each having a respective optical axis substantially parallel to said second optical axis of the second collimator doublet lens, wherein the magnification of said first and second pair right and left stereo lenses are different, wherein said base and said first and second right/left stereo lens pairs are rotatable about a pivot axis parallel to said first optical axis to selectively be in a first state wherein:

said optical axes of said first right/left stereo lens pair are each a parallel sub-component part of said optical path, and said first and second collimator doublet lenses and said first right/left stereo lens pair cooperate so that the first and second collimator doublet lenses present equal-angle chief ray pairs from symmetrically disposed object points to the lenses of first said right/left stereo lens pair, and whereby said first pair right stereo lens generates a right image at the image plane, and said first pair left stereo lens generates a left image at the image plane, such that corresponding portions of each right/left image are mapped to within a selected distance of each other, and in a second state wherein said optical axes of said second right/left stereo lens pair are each a parallel sub-component part of said optical path, and said first and second collimator doublet lenses and said second right/left stereo lens pair cooperate so that the first and second collimator doublet lenses present equal-angle chief ray pairs from symmetrically disposed object points to the lenses of said second right/left stereo lens pair, and whereby said second pair right stereo lens generates a right image at the image plane, and said second pair left stereo lens generates a left image at the image plane, such that corresponding portions of each right/left image are mapped to within a selected distance of each other.

16. A lens system according to claim 15 wherein the diameter of said second collimator doublet lens is approximately equal to the diameter of said first collimator doublet lens.

17. A lens system according to claim 16 wherein said first pair right stereo lens is substantially identical to said first pair left stereo lens, and said second pair right stereo lens is substantially identical to said second pair left stereo lens.

18. A lens system according to claim 17 wherein said first and second pair right stereo lens and said first and second left stereo lens each have a circular cross-section transverse to the respective optical axes of said first and second pair right stereo lens and said first and second pair left stereo lens.

19. A lens system according to claim 18 wherein the diameters of said first and second pair right stereo lens and said first and second pair left stereo lens are less than or equal to one-half the diameter of said first and second collimator doublet lenses, and said optical axes of said first and second pair right stereo lens and said first and second pair left stereo lens are off-set from said first and second optical axes of said first and second collimator doublet lenses by more than one-fourth the diameter of said first and second collimator doublet lenses.

20. A lens system according to claim 15 further comprises a third channel lens adjacent to said second collimator doublet lens and disposed for collecting light from said second collimator doublet lens, said third channel lens having an optical axis substantially parallel to the optical axis of said second collimator doublet lens.

21. A lens system according to claim 20 wherein the optical axis of said third channel lens is coaxial with the optical axis of said second collimator doublet lens.

22. A lens system according to claim 19 further comprises a third channel lens adjacent to said second collimator doublet lens and disposed for collecting light from said second collimator doublet lens, said third channel lens having an optical axis substantially parallel to the optical axis of said second collimator doublet lens.

23. A lens system according to claim 22 wherein the optical axis of said third channel lens is coaxial with the optical axis of said second collimator doublet lens.

* * * * *